United States Patent [19]
Kusters-Van Someren et al.

[11] Patent Number: 5,830,737
[45] Date of Patent: *Nov. 3, 1998

[54] CLONING AND EXPRESSION OF THE EXO-POLYGALACTURONASE GENE FROM ASPERGILLUS

[75] Inventors: Margo Anne-Rose Kusters-Van Someren, Bunnik; Yvonne Müller, Arnhem; Hermanus Cornelis Maria Kester, Druten; Jacob Visser, Wageningen; Albert Johannes Joseph Van Ooyen, Voorburg, all of Netherlands; Claus Rolin, Køge, Denmark

[73] Assignee: Gist-Brocades, N.V., Ma Delft, Netherlands

[ * ] Notice: The term of this patent shall not extend beyond the expiration date of Pat. No. 5,624,834.

[21] Appl. No.: 780,869

[22] Filed: Jan. 24, 1997

Related U.S. Application Data

[62] Division of Ser. No. 290,978, Oct. 17, 1994, Pat. No. 5,624,834.

[30] Foreign Application Priority Data

Dec. 24, 1992 [NL] Netherlands ................ 92204093.6

[51] Int. Cl.[6] .................... C12N 9/26; C12N 15/56
[52] U.S. Cl. ................ 435/201; 435/252.3; 435/254.3; 435/320.1; 536/23.2
[58] Field of Search ................... 435/201, 252.3, 435/254.3, 320.1; 536/23.2

[56] References Cited

FOREIGN PATENT DOCUMENTS 0 278 355 A2  8/1988  European Pat. Off. .
0 353 188 A2  1/1990  European Pat. Off. .
0 388 593 A1  9/1990  European Pat. Off. .
0 421 919     4/1991  European Pat. Off. .
91/04331      4/1991  WIPO .

OTHER PUBLICATIONS

Bussink, H. J. D. et al., *Curr. Genet.*, 19:467–474 (1991).
Hara et al., "Purification and Som Properties of Exo–polygalacturonase from *Aspergillus niger* Cultured in the Medium Containing Satsuma Mandarin Peel", *Nippon Shokuhin Kogyo Gakkaishi* 31(9):581–586 (1984).
He et al., "Molecular Cloning, Nucleotide Sequence, and Marker Exchange Mutagenesis of the Exo–Poly–α–D–Galacturonosidase–Encoding pehX Gene of *Erwina chrysanthemi* EC16", *Journal of Bacteriology* 172(9):4988–4995 (1990).
Kester et al., "Purification and Characterization of Polygalacturonases" *Biotechnology and Applied Biochemistry* 12:150–160 (1990).
Mill, "The Pactic Enzymes of *Aspergillus niger*", *Biochem. J.* 99:557–561 (1996).
Norz, "Wissenswertes über Apfelpektin (Teil I)" *ZSW May* 1985 255–265 (1985).
Norz, "Wissenswertes über Apfelpektin (Teil II)" *ZSW Jun.* 1985 303–306 (1985).
Pilnik et al., "The Biochemistry of Fruits and their Products", Academic Press (Hulme), vol. 1, 53–87 (1970).

*Primary Examiner*—Charles L. Patterson, Jr.
*Attorney, Agent, or Firm*—Morrison & Foerster

[57] ABSTRACT

The exo-polygalacturonase gene from Aspergillus is identified, and the enzyme encoded thereby is expressed. Specifically, the exo-polygalacturonase gene from *Aspergillus tubingensis* is is cloned and expressed, and DNA sequences from other Aspergillus strains that specifically hybridize therewith are identified. Novel expression vectors that comprise an exo-polygalacturonase encoding sequence, and host cells transformed therewith, are also provided. The invention further relates to the production of recombinant exo-polygalacturonase, and to the use of this protein.

19 Claims, 4 Drawing Sheets a:

5' GGIGTICCIGGCCAIACTTTAAT 3'  (3062) (non-coding strand)

(with variants: A above position, C T above; G G below)

5' ATTAAAGTITGGCCIGGIACGCC 3'  (3063) (coding strand)

(with variants: C G T A above; A C C T below)

b:

5' GGICCAATIGTICCICCATTIAAICCAATAAT 3'  (7734) (non-coding strand)

(with variants: T above, T T above; G below and G G G G below)

5' ATTATTGGITTIAATGGIGGIACIATTGGICC 3'  (3059) (coding strand)

(with variants: A A A above; C C C C C below)

c:

5' GAAGCIGCIAAIGGICCCAAGAA 3'  (3060) (coding strand)

(with variants: A A above; G C G T below)

5' TTCTTIGGICCGTTIGCIGCTTC 3'  (3061) (non-coding strand)

(with variants: T A C above)

a: derived from CB 1, residues 3-10
b: derived from CB 2, residues 2-12
c: derived from CB 3, residues 6-13

FIG. I

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: internal ( v i ) ORIGINAL SOURCE:
        ( C ) INDIVIDUAL ISOLATE: L2278

( x i ) SEQUENCE DESCRIPTION: SEQ ID NO:1:

```
Ala  Xaa  Ile  Lys  Val  Xaa  Pro  Gly  Thr  Pro  Ser  Ala
1                  5                        10
```

( 2 ) INFORMATION FOR SEQ ID NO:2:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: internal ( v i ) ORIGINAL SOURCE:
        ( C ) INDIVIDUAL ISOLATE: L1742

( x i ) SEQUENCE DESCRIPTION: SEQ ID NO:2:

```
Ile  Ile  Gly  Leu  Asn  Gly  Gly  Thr  Ile  Gly  Pro  Leu  Lys  Leu  Xaa  Tyr
1                  5                        10                       15
Ser  Pro  Gln
```

( 2 ) INFORMATION FOR SEQ ID NO:3:

( i ) SEQUENCE CHARACTERISTICS:

(A) LENGTH: 18 amino acids
(B) TYPE: amino acid
(C) STRANDEDNESS: single
(D) TOPOLOGY: linear (ii) MOLECULE TYPE: protein (iii) HYPOTHETICAL: NO (v) FRAGMENT TYPE: internal (vi) ORIGINAL SOURCE:
(C) INDIVIDUAL ISOLATE: L1743

(xi) SEQUENCE DESCRIPTION: SEQ ID NO:3:

```
Phe  Ser  Xaa  Ser  Xaa  Glu  Ala  Ala  Xaa  Gly  Pro  Lys  Lys  Xaa  Phe  Xaa
1                  5                           10                          15
Xaa  Leu
```

(2) INFORMATION FOR SEQ ID NO:4:

(i) SEQUENCE CHARACTERISTICS:
(A) LENGTH: 2974 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: ORGANISM: Aspergillus tubigensis
(B) STRAIN: NW756

(ix) FEATURE:
(A) NAME/KEY: exon
(B) LOCATION: 640..945

(ix) FEATURE:
(A) NAME/KEY: intron
(B) LOCATION: 946..1002

(ix) FEATURE:
(A) NAME/KEY: exon
(B) LOCATION: 1003..1371

(ix) FEATURE:
(A) NAME/KEY: intron
(B) LOCATION: 1372..1423

(ix) FEATURE:
(A) NAME/KEY: exon
(B) LOCATION: 1424..1480

(ix) FEATURE:
(A) NAME/KEY: intron
(B) LOCATION: 1481..1538

(ix) FEATURE:
(A) NAME/KEY: exon
(B) LOCATION: 1539..1940

(ix) FEATURE:
(A) NAME/KEY: intron
(B) LOCATION: 1941..1990

(ix) FEATURE:
(A) NAME/KEY: exon
(B) LOCATION: 1991..2092

(ix) FEATURE:
(A) NAME/KEY: intron
(B) LOCATION: 2093..2144

( i x ) FEATURE:
    ( A ) NAME/KEY: exon
    ( B ) LOCATION: 2145..2219

( i x ) FEATURE:
    ( A ) NAME/KEY: intron
    ( B ) LOCATION: 2220..2272

( i x ) FEATURE:
    ( A ) NAME/KEY: exon
    ( B ) LOCATION: 2273..2317

( i x ) FEATURE:
    ( A ) NAME/KEY: CDS
    ( B ) LOCATION: join(640..945, 1003..1371, 1424..1480,
          1539..1940, 1991..2092, 2145..2219, 2273..2317)

( i x ) FEATURE:
    ( A ) NAME/KEY: misc_feature
    ( B ) LOCATION: 640
    ( D ) OTHER INFORMATION: /note= "codon start= 640; product=
       " exo-polygalacturonase precursor"; gene= "pgaX""

( i x ) FEATURE:
    ( A ) NAME/KEY: sig_peptide
    ( B ) LOCATION: 640..705

( i x ) FEATURE:
    ( A ) NAME/KEY: mat_peptide
    ( B ) LOCATION: 706..2317

( i x ) FEATURE:
    ( A ) NAME/KEY: misc_feature
    ( B ) LOCATION: 706..2317
    ( D ) OTHER INFORMATION: /note= "IDENTIFICATION METHOD:
       experimental; product= "exo-polygalacturonase mature
       enzyme"; evidence= EXPERIMENTAL"

( x i ) SEQUENCE DESCRIPTION: SEQ ID NO:4:

```
GACTCTAGAG  GATCCCCCTG  TCGGCCTTTT  AAATGGCTTC  CTAGTGGTGG  TGTATTGTCC      60

ACGAGGCTTG  TACCACACGG  AGTTTGCACT  GACCTGCACT  TACCGCAAGT  TTCGGGAATT     120

GACCTGCGCG  ACAATATGAT  CTAACGGGGA  TTAAAGAATA  ACCGGGTATT  GCTCTCTCAA     180

TTAAAATGAA  ATCATGATGC  AGAAGATGGC  TGGGGTAAGT  TCCCTGCCAA  TTCCCCAGAA     240

ACACGTTTTT  CCCCCAATCG  GATAATCGTC  TCCGACAAGC  CCTCCTATCA  CATCGTCTCT     300

CGTTGCTCCT  CCACGCAATC  CCCCACCACC  ACATTCTCCA  GCAGCTAACT  GTCTCCAAGT     360

GCCCCTGTTG  ATTACAGGAG  CAAGCCACAA  GCTTAGCATA  GCTCCACAGC  CGTGGTGTGC     420

TCACTCCGTT  TGGTCGATTT  TGTTTCCCCG  GATATGGAGT  CCAGCGAACT  CCCCAACTCG     480

GAGACATGGG  TGGTGTGGTC  AGTGTGAGCA  AGACTGCGGG  GGAGCAATGT  CGACTCAGTG     540

CAATGGATAT  AAATGCCAGT  GGCGATCGTC  GTTGCTCTGC  GGTAATCCTG  CCCAAGCTCT     600

GTCCGTGAAC  CCAGACTTGT  CTCCTGCCAA  TTACACACA ATG AGA CTC ACG CAC          654
                                            Met Arg Leu Thr His
                                            -22         -20
```

```
GTT CTC TCG CAC ACG CTT GGC CTT CTT GCG CTA GGG GCC ACA GCA GAG           702
Val Leu Ser His Thr Leu Gly Leu Leu Ala Leu Gly Ala Thr Ala Glu
    -15              -10                      -5

GCC TTC TCC CGA TCC AGA GAA GCT GCC TGC GGC CCA AAA AAG CCT TTC           750
Ala Phe Ser Arg Ser Arg Glu Ala Ala Cys Gly Pro Lys Lys Pro Phe
    1            5                10                        15

CGG CCT CTA CCT ACA AGC CAG AGC AGG GAC AAG ACC TGC CAT GTC CGC           798
Arg Pro Leu Pro Thr Ser Gln Ser Arg Asp Lys Thr Cys His Val Arg
            20              25                      30

AGC CAT GGA GAT GGC ACT GAC GAC TCT GAT TAC ATT CTC TCC GCA TTG           846
Ser His Gly Asp Gly Thr Asp Asp Ser Asp Tyr Ile Leu Ser Ala Leu
        35              40                      45
```

| | | | | | | | | | | | | | | | | |
|---|---|---|---|---|---|---|---|---|---|---|---|---|---|---|---|---|
| AAC | CAA | TGT | AAC | CAC | GGT | GGA | AAG | GTA | GTT | TTT | GAT | GAG | GAC | AAG | GAA | 894 |
| Asn | Gln | Cys | Asn | His | Gly | Gly | Lys | Val | Val | Phe | Asp | Glu | Asp | Lys | Glu | |
| | | | 50 | | | | 55 | | | | | 60 | | | | |
| TAC | ATT | ATC | GGG | ACG | GCA | CTG | AAT | ATG | ACC | TTC | CTG | AAG | AAC | ATT | GAC | 942 |
| Tyr | Ile | Ile | Gly | Thr | Ala | Leu | Asn | Met | Thr | Phe | Leu | Lys | Asn | Ile | Asp | |
| | 65 | | | | 70 | | | | 75 | | | | | | | |

CTA GGTGCTTATT CTGCAGACCC AATCAAGGTG ACCATTGACT AACCTTATGG TTCAACA 1002
Leu
80

| | | | | | | | | | | | | | | | | |
|---|---|---|---|---|---|---|---|---|---|---|---|---|---|---|---|---|
| GAG | GTC | CTC | GGA | ACA | ATC | TTA | TTC | ACT | AAC | GAT | ACA | GAC | TAC | TGG | CAA | 1050 |
| Glu | Val | Leu | Gly | Thr | Ile | Leu | Phe | Thr | Asn | Asp | Thr | Asp | Tyr | Trp | Gln | |
| | | | | 85 | | | | | 90 | | | | | 95 | | |
| GCC | AAC | TCC | TTC | AAA | CAG | GGC | TTC | CAG | AAC | GCT | ACG | ACC | TTC | TTC | CAA | 1098 |
| Ala | Asn | Ser | Phe | Lys | Gln | Gly | Phe | Gln | Asn | Ala | Thr | Thr | Phe | Phe | Gln | |
| | | | | 100 | | | | | 105 | | | | | 110 | | |
| CTC | GGT | GGT | GAA | GAT | GTG | AAT | ATG | TAC | GGT | GGT | GGT | ACA | ATC | AAT | GGC | 1146 |
| Leu | Gly | Gly | Glu | Asp | Val | Asn | Met | Tyr | Gly | Gly | Gly | Thr | Ile | Asn | Gly | |
| | | | 115 | | | | | 120 | | | | | 125 | | | |
| AAC | GGA | CAG | GTC | TGG | TAT | GAT | CTG | TAT | GCC | GAA | GAT | GAT | CTC | ATT | CTG | 1194 |
| Asn | Gly | Gln | Val | Trp | Tyr | Asp | Leu | Tyr | Ala | Glu | Asp | Asp | Leu | Ile | Leu | |
| | 130 | | | | | 135 | | | | | 140 | | | | | |
| CGT | CCC | ATC | TTG | ATG | GGC | ATC | ATT | GGG | CTG | AAT | GGT | GGC | ACA | ATT | GGT | 1242 |
| Arg | Pro | Ile | Leu | Met | Gly | Ile | Ile | Gly | Leu | Asn | Gly | Gly | Thr | Ile | Gly | |
| 145 | | | | | 150 | | | | | 155 | | | | | 160 | |
| CCG | CTG | AAG | CTG | CGG | TAC | TCG | CCG | CAA | TAC | TAC | CAT | TTT | GTG | GCT | AAC | 1290 |
| Pro | Leu | Lys | Leu | Arg | Tyr | Ser | Pro | Gln | Tyr | Tyr | His | Phe | Val | Ala | Asn | |
| | | | | 165 | | | | | 170 | | | | | 175 | | |
| TCG | TCG | AAT | GTG | CTC | TTT | GAC | GGG | ATT | GAC | ATT | TCG | GGT | TAT | AGT | AAG | 1338 |
| Ser | Ser | Asn | Val | Leu | Phe | Asp | Gly | Ile | Asp | Ile | Ser | Gly | Tyr | Ser | Lys | |
| | | | 180 | | | | | 185 | | | | | 190 | | | |
| AGC | GAC | AAC | GAA | GCC | AAA | AAC | ACT | GAT | GGA | TGG | TGCGTTTTAT CCTGCTTTAC | | | | | 1391 |
| Ser | Asp | Asn | Glu | Ala | Lys | Asn | Thr | Asp | Gly | Trp | | | | | | |
| | | 195 | | | | | 200 | | | | | | | | | |

ACTGAGCGTT ATACTGACCT TTTTCCCGTA GG GAT ACC TAC CGC TCG AAC AAT 1444
                                    Asp Thr Tyr Arg Ser Asn Asn
                                        205             210

| | | | | | | | | | | | |
|---|---|---|---|---|---|---|---|---|---|---|---|
| ATC | GTT | ATC | CAG | AAT | TCG | GTG | ATC | AAC | AAC | GGT | GAT GGTAAGTTAA | 1490 |
| Ile | Val | Ile | Gln | Asn | Ser | Val | Ile | Asn | Asn | Gly | Asp | |
| | | | 215 | | | | | 220 | | | | |

ACCTAAGTAG CGTCATACTT CAACAATTCT AACCTGCAAA CCTACACA GAC TGT GTC 1547
                                                    Asp Cys Val
                                                        225

| | | | | | | | | | | | | | | | | |
|---|---|---|---|---|---|---|---|---|---|---|---|---|---|---|---|---|
| TCT | TTC | AAG | CCG | AAC | AGC | ACC | AAT | ATC | CTC | GTT | CAG | AAC | CTT | CAC | TGC | 1595 |
| Ser | Phe | Lys | Pro | Asn | Ser | Thr | Asn | Ile | Leu | Val | Gln | Asn | Leu | His | Cys | |
| | | | | 230 | | | | | 235 | | | | | 240 | | |
| AAT | GGC | TCC | CAC | GGC | ATT | TCT | GTT | GGC | TCT | CTC | GGC | CAA | TAC | AAG | GAT | 1643 |
| Asn | Gly | Ser | His | Gly | Ile | Ser | Val | Gly | Ser | Leu | Gly | Gln | Tyr | Lys | Asp | |
| | | | 245 | | | | | 250 | | | | | 255 | | | |
| GAG | GTT | GAC | ATC | GTT | GAG | AAT | GTC | TAT | GTG | TAC | AAC | ATC | TCT | ATG | TTT | 1691 |
| Glu | Val | Asp | Ile | Val | Glu | Asn | Val | Tyr | Val | Tyr | Asn | Ile | Ser | Met | Phe | |
| | | 260 | | | | | 265 | | | | | 270 | | | | |
| AAT | GCT | TCG | GTA | TGT | CTG | AAC | TTT | AAC | CAT | ATA | ATA | GAC | TTC | TTA | CTA | 1739 |
| Asn | Ala | Ser | Val | Cys | Leu | Asn | Phe | Asn | His | Ile | Ile | Asp | Phe | Leu | Leu | |
| 275 | | | | | 280 | | | | | 285 | | | | | | |
| ACT | TGG | TTG | CAG | GAT | ATG | GCC | CGC | ATC | AAG | GTT | TGG | CCT | GGT | ACT | CCC | 1787 |
| Thr | Trp | Leu | Gln | Asp | Met | Ala | Arg | Ile | Lys | Val | Trp | Pro | Gly | Thr | Pro | |
| 290 | | | | | 295 | | | | | 300 | | | | | 305 | |
| TCT | GCG | CTA | TCT | GCC | GAT | CTT | CAA | GGC | GGC | GGT | GGC | TCG | GGT | AGC | GTA | 1835 |
| Ser | Ala | Leu | Ser | Ala | Asp | Leu | Gln | Gly | Gly | Gly | Gly | Ser | Gly | Ser | Val | |
| | | 310 | | | | | 315 | | | | | 320 | | | | |

-continued

```
AAG  AAT  ATC  ACC  TAT  GAC  ACC  GCA  CTC  ATT  GAT  AAT  GTC  GAC  TGG  GCC          1883
Lys  Asn  Ile  Thr  Tyr  Asp  Thr  Ala  Leu  Ile  Asp  Asn  Val  Asp  Trp  Ala
               325                     330                     335

ATT  GAA  ATC  ACG  CAG  TGC  TAT  GGG  CAG  AAG  AAT  ACT  ACC  TTG  TGC  AAC          1931
Ile  Glu  Ile  Thr  Gln  Cys  Tyr  Gly  Gln  Lys  Asn  Thr  Thr  Leu  Cys  Asn
          340                     345                     350

GAG  TAC  CCG  GTTAGTAGAC  CTTCAGCCGC  TTTCCCGAAG  CTATCCTAAT                            1980
Glu  Tyr  Pro
          355

ACAATAATAG  AGC  CTC  CTC  ACC  ATC  TCG  GAC  GTC  CAC  ATC  AAG  AAC  TTC             2029
            Ser  Ser  Leu  Thr  Ile  Ser  Asp  Val  His  Ile  Lys  Asn  Phe
                            360                     365

CGC  GGT  ACG  ACG  TCG  GGA  TCG  GAA  GAT  CCC  TAT  GTT  GGG  ACA  ATT  GTT          2077
Arg  Gly  Thr  Thr  Ser  Gly  Ser  Glu  Asp  Pro  Tyr  Val  Gly  Thr  Ile  Val
370                     375                     380                     385

TGT  TCC  AGT  CCT  GAT  GTAAGTGCCC  TCCAGGATAT  GCGTTTAGTG  TGCAATGGCT                  2132
Cys  Ser  Ser  Pro  Asp
               390

GACACTCGAT  AG  ACT  TGC  TCG  GAT  ATC  TAT  ACT  TCC  AAT  ATT  AAT  GTA              2180
                Thr  Cys  Ser  Asp  Ile  Tyr  Thr  Ser  Asn  Ile  Asn  Val
                                    395                     400

ACA  AGC  CCG  GAT  GGA  ACC  AAC  GAC  TTT  GTT  TGC  GAT  AAT  GTGAGTCGGC              2229
Thr  Ser  Pro  Asp  Gly  Thr  Asn  Asp  Phe  Val  Cys  Asp  Asn
          405                     410                     415

CAAGGCCAGG  TGAAGATCTA  AATCGGTGAC  TAACGCTGTC  CAG  GTC  GAT  GAG  AGT                  2284
                                                 Val  Asp  Glu  Ser

CTT  CTG  AGT  GTC  AAC  TGC  ACC  GCC  ACT  TCT  GAT  TAAGTTAGAA  TGCCTGTTAA            2337
Leu  Leu  Ser  Val  Asn  Cys  Thr  Ala  Thr  Ser  Asp
420                     425                     430

CATGTACACT  GGAGGTCAGG  CCTTACTTAG  ACGGATGAAG  GGTGTATATA  TTCACTTTGG                   2397

GTTCGGCTGT  GTATATACGT  GAGCAAATAA  TATCTGTATG  CTTTTGACTT  AGGGAAGGTC                   2457

AGGCGATCAA  GTAACTTTCT  GGTTCAAACC  TTGATCATGG  TTCTCAGTAG  ACGCTCCTTC                   2517

TGCTTTTTGC  GTTGCGATAC  GTCACATGCC  GAGGGAAGAA  TCATTGCTTC  CAGGTGCTTG                   2577

CGCTCTCCTG  AGTGATACTG  CACTTGCTGT  CCAGGATACT  ACATCTCTCT  GCATTTACCT                   2637

GCTGTTCATC  AAACAAGCAA  GCAACCTGAA  GAGCCACCTA  CCAAGTATAG  TAGGATCTAG                   2697

AGCGCTCCGA  GGAGATCGTG  TAGACCATAC  TAGATCCTCG  AAAATGTAAA  TTGCAAACCA                   2757

TATTTCAATT  CTAATTCATC  TGAAGTCTGG  CAGCGAGATA  TATAACCGAA  GTCTCTTGGA                   2817

ACACGAACCC  TCGGCTGATG  ATCGTGACCT  CCTGAGTAGC  ACCCAACCAG  CGGACTACAA                   2877

GATGGACAAC  GAACCTTACC  CACAACCCTT  AAGTACTTTG  GAACCAAGTG  GCAATGATTT                   2937

GTATTCTTTA  TCGGTGTGCG  TCATGCACCT  CCTGCAG                                              2974
```

( 2 ) INFORMATION FOR SEQ ID NO:5:

( i ) SEQUENCE CHARACTERISTICS:
        ( A ) LENGTH: 452 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met  Arg  Leu  Thr  His  Val  Leu  Ser  His  Thr  Leu  Gly  Leu  Leu  Ala  Leu
-22       -20                     -15                     -10

Gly  Ala  Thr  Ala  Glu  Ala  Phe  Ser  Arg  Ser  Arg  Glu  Ala  Ala  Cys  Gly
          -5                     1                  5                      10

Pro  Lys  Lys  Pro  Phe  Arg  Pro  Leu  Pro  Thr  Ser  Gln  Ser  Arg  Asp  Lys
```

```
                                  15                          20                          25
Thr  Cys  His  Val  Arg  Ser  His  Gly  Asp  Gly  Thr  Asp  Asp  Ser  Asp  Tyr
               30                       35                       40

Ile  Leu  Ser  Ala  Leu  Asn  Gln  Cys  Asn  His  Gly  Gly  Lys  Val  Val  Phe
               45                       50                       55

Asp  Glu  Asp  Lys  Glu  Tyr  Ile  Ile  Gly  Thr  Ala  Leu  Asn  Met  Thr  Phe
          60                       65                       70

Leu  Lys  Asn  Ile  Asp  Leu  Glu  Val  Leu  Gly  Thr  Ile  Leu  Phe  Thr  Asn
75                       80                       85                            90

Asp  Thr  Asp  Tyr  Trp  Gln  Ala  Asn  Ser  Phe  Lys  Gln  Gly  Phe  Gln  Asn
                    95                       100                      105

Ala  Thr  Thr  Phe  Phe  Gln  Leu  Gly  Gly  Glu  Asp  Val  Asn  Met  Tyr  Gly
               110                      115                      120

Gly  Gly  Thr  Ile  Asn  Gly  Asn  Gly  Gln  Val  Trp  Tyr  Asp  Leu  Tyr  Ala
          125                      130                      135

Glu  Asp  Asp  Leu  Ile  Leu  Arg  Pro  Ile  Leu  Met  Gly  Ile  Ile  Gly  Leu
     140                      145                      150

Asn  Gly  Gly  Thr  Ile  Gly  Pro  Leu  Lys  Leu  Arg  Tyr  Ser  Pro  Gln  Tyr
155                      160                      165                           170

Tyr  His  Phe  Val  Ala  Asn  Ser  Ser  Asn  Val  Leu  Phe  Asp  Gly  Ile  Asp
                    175                      180                      185

Ile  Ser  Gly  Tyr  Ser  Lys  Ser  Asp  Asn  Glu  Ala  Lys  Asn  Thr  Asp  Gly
               190                      195                      200

Trp  Asp  Thr  Tyr  Arg  Ser  Asn  Asn  Ile  Val  Ile  Gln  Asn  Ser  Val  Ile
          205                      210                      215

Asn  Asn  Gly  Asp  Asp  Cys  Val  Ser  Phe  Lys  Pro  Asn  Ser  Thr  Asn  Ile
     220                      225                      230

Leu  Val  Gln  Asn  Leu  His  Cys  Asn  Gly  Ser  His  Gly  Ile  Ser  Val  Gly
235                      240                      245                           250

Ser  Leu  Gly  Gln  Tyr  Lys  Asp  Glu  Val  Asp  Ile  Val  Glu  Asn  Val  Tyr
                    255                      260                      265

Val  Tyr  Asn  Ile  Ser  Met  Phe  Asn  Ala  Ser  Val  Cys  Leu  Asn  Phe  Asn
               270                      275                      280

His  Ile  Ile  Asp  Phe  Leu  Leu  Thr  Trp  Leu  Gln  Asp  Met  Ala  Arg  Ile
          285                      290                      295

Lys  Val  Trp  Pro  Gly  Thr  Pro  Ser  Ala  Leu  Ser  Ala  Asp  Leu  Gln  Gly
     300                      305                      310

Gly  Gly  Gly  Ser  Gly  Ser  Val  Lys  Asn  Ile  Thr  Tyr  Asp  Thr  Ala  Leu
315                      320                      325                           330

Ile  Asp  Asn  Val  Asp  Trp  Ala  Ile  Glu  Ile  Thr  Gln  Cys  Tyr  Gly  Gln
                    335                      340                      345

Lys  Asn  Thr  Thr  Leu  Cys  Asn  Glu  Tyr  Pro  Ser  Ser  Leu  Thr  Ile  Ser
               350                      355                      360

Asp  Val  His  Ile  Lys  Asn  Phe  Arg  Gly  Thr  Thr  Ser  Gly  Ser  Glu  Asp
          365                      370                      375

Pro  Tyr  Val  Gly  Thr  Ile  Val  Cys  Ser  Ser  Pro  Asp  Thr  Cys  Ser  Asp
     380                      385                      390

Ile  Tyr  Thr  Ser  Asn  Ile  Asn  Val  Thr  Ser  Pro  Asp  Gly  Thr  Asn  Asp
395                      400                      405                           410

Phe  Val  Cys  Asp  Asn  Val  Asp  Glu  Ser  Leu  Leu  Ser  Val  Asn  Cys  Thr
                    415                      420                      425

Ala  Thr  Ser  Asp
               430
```

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: pki SmaI sense ( x i ) SEQUENCE DESCRIPTION: SEQ ID NO:6:

TTTTCCTTCC CGGGCAC         17

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
        ( C ) INDIVIDUAL ISOLATE: pki-pgaX antisense ( x i ) SEQUENCE DESCRIPTION: SEQ ID NO:7:

GTGCGTGAGT CTCATCTTGA CGGATGATTG         30

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: pki-pgaX sense ( x i ) SEQUENCE DESCRIPTION: SEQ ID NO:8:

CAATCATCCG TCAAGATGAG ACTCACGCAC         30

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES (v i) ORIGINAL SOURCE:
                (C) INDIVIDUAL ISOLATE: pgaX NcoI antisense (x i) SEQUENCE DESCRIPTION: SEQ ID NO:9:

AGTGCCATCT CCATGGC                                                                                          17

(2) INFORMATION FOR SEQ ID NO:10:

(i) SEQUENCE CHARACTERISTICS:
                (A) LENGTH: 23 base pairs
                (B) TYPE: nucleic acid
                (C) STRANDEDNESS: single
                (D) TOPOLOGY: linear (i i) MOLECULE TYPE: DNA (genomic)

(i i i) HYPOTHETICAL: NO (i v) ANTI-SENSE: YES (v i) ORIGINAL SOURCE:
                (C) INDIVIDUAL ISOLATE: 3062

(i x) FEATURE:
                (A) NAME/KEY: misc_feature
                (B) LOCATION: one-of(3, 6, 9, 15)
                (D) OTHER INFORMATION: /note= "N at position 3, 6, 9, and
                        15 is inosine"

(x i) SEQUENCE DESCRIPTION: SEQ ID NO:10:

GGNGTNCCNG GVCANACYTT DAT                                                                                   23

(2) INFORMATION FOR SEQ ID NO:11:

(i) SEQUENCE CHARACTERISTICS:
                (A) LENGTH: 23 base pairs
                (B) TYPE: nucleic acid
                (C) STRANDEDNESS: single
                (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
                (C) INDIVIDUAL ISOLATE: 3063

(i x) FEATURE:
                (A) NAME/KEY: misc_feature
                (B) LOCATION: one-of(9, 15, 18)
                (D) OTHER INFORMATION: /note= "N at position 9, 15, and 18
                        is inosine"

(x i) SEQUENCE DESCRIPTION: SEQ ID NO:11:

ATHAARGTNT GBCCNGGNAC NCC                                                                                   23

(2) INFORMATION FOR SEQ ID NO:12:

(i) SEQUENCE CHARACTERISTICS:
                (A) LENGTH: 32 base pairs
                (B) TYPE: nucleic acid
                (C) STRANDEDNESS: single
                (D) TOPOLOGY: linear (i i) MOLECULE TYPE: DNA (genomic)

(i i i) HYPOTHETICAL: NO (i v) ANTI-SENSE: YES (v i) ORIGINAL SOURCE:

(C) INDIVIDUAL ISOLATE: HR7734

(ix) FEATURE:
  (A) NAME/KEY: misc_feature
  (B) LOCATION: one-of(3, 9, 12, 15, 21, 23)
  (D) OTHER INFORMATION: /note= "N at position 3, 9, 12, 15, 21, and 23 is inosine"

(xi) SEQUENCE DESCRIPTION: SEQ ID NO:12:

GGNCCDATNG TNCCNCCRTT NARNCCDATD AT    32

(2) INFORMATION FOR SEQ ID NO:13:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (C) INDIVIDUAL ISOLATE: 3059

(ix) FEATURE:
    (A) NAME/KEY: misc_feature
    (B) LOCATION: one-of(9, 12, 18, 21, 24, 30)
    (D) OTHER INFORMATION: /note= "N at position 9, 12, 18, 21, 24, and 30 is inosine"

(xi) SEQUENCE DESCRIPTION: SEQ ID NO:13:

ATHATHGGNY TNAAYGGNGG NACNATHGGN CC    32

(2) INFORMATION FOR SEQ ID NO:14:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (C) INDIVIDUAL ISOLATE: 3060

(ix) FEATURE:
    (A) NAME/KEY: misc_feature
    (B) LOCATION: one-of(6, 9, 12, 15)
    (D) OTHER INFORMATION: /note= "N at position 6, 9, 12, and 15 is inosine"

(xi) SEQUENCE DESCRIPTION: SEQ ID NO:14:

GAGGCNGCNA CNGGNCCNAA GAA    23

(2) INFORMATION FOR SEQ ID NO:15:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO

```
( i v ) ANTI-SENSE: YES ( v i ) ORIGINAL SOURCE:
        ( C ) INDIVIDUAL ISOLATE: 3061

( i x ) FEATURE:
        ( A ) NAME/KEY: misc_feature
        ( B ) LOCATION: one-of(6, 9, 15)
        ( D ) OTHER INFORMATION: /note= "N at position 6, 9, and 15
              is inosine"

( x i ) SEQUENCE DESCRIPTION: SEQ ID NO:15:

TTYTTNGGNC CRTTNGCNGC YTC                                                                          2 3
```

CLONING AND EXPRESSION OF THE EXO-POLYGALACTURONASE GENE FROM ASPERGILLUS

This application is a divisional of application Ser. No. 08/290,978 filed 17 Oct. 1994, now U.S. Pat. No. 5,624,834.

TECHNICAL FIELD

The present invention is in the field of molecular biology. Specifically, a DNA sequence encoding the exo-polygalacturonase gene from Aspergillus is cloned and expressed. The invention relates to vectors comprising the exo-polygalacturonase coding sequence and to host cells transformed with such vectors. The invention further relates to the production of recombinant exo-polygalacturonase. Furthermore, as an example of the application of this enzyme partial pectin degradation is demonstrated.

BACKGROUND OF THE INVENTION

Pectins are major constituents of the cell walls of edible parts of fruits and vegetables. The middle lamella which are situated between the cell walls are mainly built up from protopectin which is in the insoluble form of pectin. Pectins are considered as intercellular adhesives and due to their colloid nature they also have an important function in the water-regulation of plants. Water-binding capacity is greatly increased by the amount of hydrophylic hydroxyl and carboxyl groups. The amount of pectin can be very high. For example, lemon peels are reported to contain pectin up to 30% of their dry weight, orange peels contain from 15–20% and apple peels about 10% (Norz, K., 1985. Zucker und Süsswaren Wirtschaft 38 5–6).

Pectins are composed of a rhamno-galacturonan backbone in which 1,4-linked α-D-galacturonan chains are interrupted at intervals by the insertion of 1,2-linked α-L-rhamnopyranosyl residues (Pilnik, W. and A. Voragen 1970. In 'The Biochemistry of fruits and their products', Vol. 1, Chapter 3, p.53. Acad. Press). Other sugars, such as D-galactose, L-arabinose and D-xylose, are present as side chains. A large part of the galacturonan residues is esterified with methyl groups at the C2 and C3 position.

Pectin-degrading enzymes are important tools in the food industry. Traditionally these enzymes are used as mixtures. *Aspergillus niger* and other fungi produce a whole spectrum of enzymes which can advantageously be used in the degradation of pectin. Examples of such enzymes are pectin esterase, pectin lyase (also called pectin transeliminase), endo- and exo-polygalacturonases. In *A. niger* the pectin degrading proteins are not expressed constitutively. Induction of these enzymes is achieved by growing the strains when carbon sources such as glucose or sucrose are limiting and in the presence of pectin or breakdown products thereof.

In order to avoid the problem of induction and also to avoid obtaining not well-defined enzyme mixtures there is a growing tendency to clone the genes encoding these enzymes and to express them in other more suitable host cells.

The cloning and expression of several of these enzymes obtained from *Aspergillus niger* has been reported. EP 0 278 355 describes the cloning of the pectin lyase gene, the sequence thereof and the expression. EP 0 353 188 adds some other pectin lyases.

As mentioned above pectin contains a backbone comprising a high amount of 1,4-linked α-D-galacturonan molecules. This backbone can be digested by the action of depolymerases. Two such depolymerases are known, endo- and exo-polygalacturonase. Examples of the cloning and expression of especially the former one of these depolymerases have been reported, EO 0 421 919 discloses two polygalacturonases which can be classified as endo-polygalacturonases. Another endo-polygalacturonase has been disclosed in EP 0 388 593. Both of these patent application used Aspergilli as the source of the gene.

Exo-polygalacturonases are not so abundant as the endo-form as evidenced by the reports about this enzyme published so far.

Mill (Biochem. J. 99: 557–561 and 562–565 (1966)) reported the isolation and characterization of two distinct exo-polygalacturonases. One of these was found to be mercury activated. This was confirmed by Hara et al. (Nippon Shokuhim Kogyo Gakkashi 31: 581–586 (1984)). Kester and Visser (Biotechn. Appl. Biochem, 12: 150–160 (1990)) report the presence of only one exo-polygalacturonase and 5 endo-polygalacturonases in *A. niger* culture filtrates. Finally, the cloning of exo-polygalacturonase from *Erwinia chrysanthemi* EC16 has been reported (He and Collmer J. Bacteriol. 172: 4988–4995 (1990)).

Exo-polygalacturonase is capable of converting polygalacturonides to galacturonic acid. To enhance this process it is advantageous to use pure exo-polygalacturonase. Galacturonic acid can be used as a source for different synthetic reactions it has for example been found to be useful in the production of ascorbic acid.

SUMMARY OF THE INVENTION

The present invention provides an isolated recombinant DNA sequence encoding exo-polygalacturonase. Preferably the exo-polygalacturonase is obtained from Aspergilli, more preferably it is obtained from *Aspergillus tubigensis* or from *Aspergillus niger*.

The invention also provides an expression cassette containing a DNA sequence encoding the exo-polygalacturonase. Such an expression cassette contains appropriate regulatory regions i.e. a promoter, optionally an enhancer, a terminator. The cassette may also contain a selection marker encoding gene.

In a further aspect of the invention the expression cassette forms part of a vector.

The invention also provides recombinant host cells transformed with the vector containing the exo-polygalacturonase encoding DNA.

The invention further provides isolated recombinant exo-polygalacturonase.

The invention also discloses a method for the production of exo-polygalacturonases. The invention shows how the exo-polygalacturonase can be purified.

The invention further discloses a method for obtaining galacturonic acid comprising the use of exo-polygalacturonase.

Finally, the invention describes the use of exo-polygalacturonase in the treatment of pectin.

DESCRIPTION OF THE FIGURES

FIG. 1 shows the oligonucleotide mixtures derived from N-terminal amino acid sequences from cyanogen bromide fragments of *A. tubigensis* exo-polygalacturonase PGX. These DNA probes have been used in hybridization experiments to detect the pgaX gene.

Figure 2:
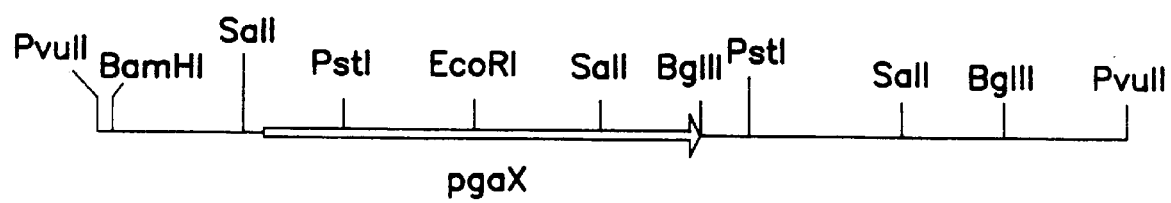
FIG. 2 shows the restriction map of the *A. tubigensis* pgaX gene. The open arrow indicates the location and orientation of the gene.

o=Rohament PL, +=exo-PG ¤=average of blanks.

DETAILED DESCRIPTION OF THE INVENTION

The present invention discloses purified and isolated DNA sequences which encode a polypeptide having the activity of the *Aspergillus tubigensis* PGX enzyme the sequence is characterized in that it comprises the sequence of SEQ ID NO: 4, genetic variants of the sequence of SEQ ID NO: 4 are likewise considered to be part of the invention as are DNA sequences encoding for the same amino acid sequence but altered making use of the degeneracy of the genetic code. Further included in the present invention are DNA sequences capable of hybridizing with the sequence of SEQ ID NO: 4 or with parts thereof.

The invention also discloses DNA constructs containing a DNA sequence encoding PGX wherein the protein encoding sequence is operably linked to regulatory regions capable of directing the expression of said DNA sequence in a suitable host organism.

The invention further discloses DNA vectors containing the DNA constructs encoding PGX.

Transformed microbial host cells containing the vectors are disclosed and the host cells are shown to produce exo-polygalacturonase under suitable growth conditions.

The present invention discloses a method for obtaining expression of exo-polygalacturonase comprising, culturing the microbial host under conditions wherein the cloned gene is expressed. A method is also disclosed for obtaining exo-polygalacturonase comprising the steps of culturing the transformed microbial host under conditions giving rise to the expression of the DNA sequence of and recovering the polypeptide.

The invention also discloses the use of a polypeptide obtained through the expression of the cloned pgaX gene to degrade pectin. It is shown in the present invention that the pectin can be specifically treated using the exo-polygalacturonase. It is disclosed that this enzyme reduces the calcium sensitivity without at the same time reducing the molecular weight of pectin.

Furthermore, the invention provides purified and isolated expression and transcription regulatory regions as found in the 5'non-coding sequences of the *Aspergillus tubigensis* pgaX gene.

The present invention describes a method for obtaining a gene encoding an Aspergillus exo-polygalacturonase. The method can be summarized as follows.

An Aspergillus strain, which may be selected from the group comprising *A. niger, A. awamori* and *A. tubigensis* is grown under conditions wherein the carbon source is limited and wherein pectin or fragments thereof are offered as substrate. These growth conditions give rise to the production of pectin degrading enzymes.

Following sufficient growth time allowing for the accumulation of the different enzymes the cells are harvested and the enzymes are isolated from the medium. After suitable identification the exo-polygalacturonase is purified and sequenced. This sequencing may be performed on the complete protein molecule it may however also be performed on fragments obtained after separation of the peptides following peptidase digestion of the complete protein.

Once the amino acid sequence or parts thereof are determined, suitable sequences are selected for choosing DNA probes. The probes are used against a genomic library of the desired Aspergillus strain. The hybridizing clones are selected and the DNA fragments contained therein are sequenced. The sequence is further completed by adding the rest of the sequence.

Suitable expression regulating sequences are then cloned upstream from the coding region. This depends on the preferred expression host cell. Expression is thus made constitutive.

The cloned gene is expressed and the medium can be used as such in the degradation of pectin. Preferably, the protein is isolated and used in the desired process.

Alternative ways for cloning, detecting, screening and expressing the gene are known and are expected to give similar results. Along these methods are methods using expression cloning combined with immunological detection, another method would be the use of PCR to amplify the DNA encoding the exo-polygalacturonase gene, this presupposes however that at least a part of the gene sequence is known.

Reaction of the exo-polygalacturonase of the present invention with pectin or pectin-like substrates gives rise to the production of galacturonic acids in monomeric or dimeric form. Galacturonic acid can for example be used in the synthesis of ascorbic acid. Unlike known processes the use of exo-polygalacturonase in pure form gives rise to less by-product formation.

Furthermore, the exo-polygalacturonase of the present invention can be used in combination with pectinesterase, pectinase and other pectin degrading enzymes. It is further shown in the examples that exo-polygalacturonase can be used to treat pectin during this treatment the viscosity of the pectin is reduced without reducing the molecular weight of this polymer.

EXPERIMENTAL

Throughout this description the following strains and vectors are employed:
Strains:
*E. coli* JM101 (Yanisch-Perron et al., 1985): thi, Δ(lac-supE, pro AB), [F', traD36, pro AB, lacI$^q$ZΔM15]
*E. coli* LE 392 (Murray, 1977): F$^-$ hsdR574 ($r_k^+$,$m_k^+$), sup44, supF58, lacY1, or Δ(lac1ZY)6, galK2, galT22, metB1, trpR55, λ$^-$
*Aspergillus niger* N402:cspA1
*Aspergillus niger* N593: cspA1, pyrA6
*Aspergillus tubigensis* NW756
*Aspergillus nidulans* G191: pabaA1, pyrG89, fwA1, uaY9
Vectors:
pEMBL18/pEMBL19 (Dente et al., 1983)

Example 1
Purification and characterization of *Aspergillus tubigensis* exo-polygalacturonase PGS

Example 1.1
Purification of *Aspergillus tubigensis* exo-polygalacturonase PGX A culture filtrate (3000 ml) was obtained by the culturing of *Aspergillus niger* strain NW756 (later reclassified as more likely belonging to the species A. tubigensis (Kusters-van Someren et al. (1991)) in a medium containing (per liter) 7.5 g $NH_4NO_3$, 1.5 g $KH_2PO4$, 0.5 g KCl, 0.5 g $MgSO_4.7H_2O$, 2 g yeast extract, trace elements according to Vishniac and Santer (1957) and 10 g degraded polygalacturonic acid as carbon source, pH 6.0.

Polygalacturonic acid was degraded as follows: 40 g polygalacturonic acid (United States Biochemical Corp.) was dissolved in two liters 20 mM sodium acetate buffer pH 4.8 and incubated with 4000 Units of purified A. niger endopolygalacturonase II, of which the purification is described by Kester and Visser (1990), for 24 hours at 30° C.

The pH of the medium was adjusted to 6.0 following inoculation at $10^6$ spores/ml and incubation at 30° C. in an orbital shaker at 250 rpm for 55 hours. The culture fluid was passed through cheese cloth and the filtrate was brought to 10 mM sodium acetate, adjusted to pH 4.0 and loaded on a crosslinked alginate column (100 ml) in 20 mM sodium acetate buffer pH 4.0.

The non-bound fraction which contained a mixture of residual endo-PG activity and exo-polygalacturonase activity was concentrated by batch wise adsorption on DEAE Sephadex A-50 (200 g wet weight) at pH 6.0 followed by pulse elution with 1M NaCl in 20 mM sodium phosphate buffer pH 6.0 and dialysis against the same buffer without the salt. The dialysate was loaded on a DEAE-Sepharose Fast Flow column (2.5×10 cm) equilibrated in 10 mM bisTris/HCl buffer pH 5.5.

After elution with a 800 ml linear sodium chloride gradient (0–0.5M), fractions were assayed for polygalacturonase activity and screened for exo-polygalacturonase activity by a TLC method. This method consists of incubation of samples of the column fractions with 1% (w/v) polygalacturonic acid in 0.1M sodium acetate buffer pH 4.2 at 30° C. followed by analysis of the reaction products by thin layer chromatography as described by Kester and Visser (1990).

Exo-polygalacturonase positive fractions were pooled, dialyzed against 20 mM sodium acetate buffer pH 4.0 and loaded on a S-Sepharose Fast Flow column (2.5×7 cm) equilibrated in the same buffer. Elution was done with a 600 ml linear sodium chloride gradient (0–0.5M).

Final purification was accomplished by repeated chromatography on a MONO Q column (Pharmacia, Uppsala, Sweden) in 20 mM piperazine/HCl buffer pH 6.0. Exo-polygalacturonase containing fractions were diluted five times with water loaded on the column and eluted with a 40 ml linear sodium chloride gradient (0–0.2M) at a flow rate of 2 ml/minute. A summary of the specific activity and recovery of the enzyme during purification is given in Table I.

TABLE I

Purification of exo-polygalacturonase PGX from A. tubigensis NW756

| Step | Total Volume (ml) | Total activity (units) | protein (mg) | Specific activity (units/mg) | Yield (%) |
|---|---|---|---|---|---|
| Culture fluid | 3000 | 5230 | 300 | 17.4 | 100 |
| Crosslinked | 210 | 3100 | 212 | 14.6 | 59 |

TABLE I-continued

Purification of exo-polygalacturonase PGX from A. tubigensis NW756

| Step | Total Volume (ml) | Total activity (units) | protein (mg) | Specific activity (units/mg) | Yield (%) |
|---|---|---|---|---|---|
| alginate DEAE-Sepharose | 90 | 846 | 98 | 8.6 | 16 |
| S-Sepharose | 72 | 188 | 8.8 | 21.4 | 3.6 |
| MONO Q | 10.8 | 121 | 3.1 | 39.0 | 2.3 |

Polygalacturonase activity was determined by measuring the release of reducing sugars in a reaction mixture containing 0.25% (w/v) polygalacturonic acid in 0.1M sodium acetate buffer pH 4.2 at 30° C. Reducing end groups were determined by the neocuproine method described by Stephens et al. (1974). One activity unit was defined as the amount of enzyme which produces one $\mu$mole of reducing sugars per minute.

The apparent molecular mass of exo-polygalacturonase PGX, as determined by SDS-PAGE on a 10% gel, was 78 kDa. After deglycosylation of the enzyme with N-glycanase (Genzyme, Cambridge, Mass.) according to the supplier instructions the molecular weight was reduced to 52 kDa.

Isoelectric focussing resulted in five distinct bands, all showing exo-polygalacturonase activity, in the pH range 3.7–4.4.

Example 1.2

Amino acid sequence determination of the N-termini of cyanogen bromide released peptides of exo-polygalacturonase PGX Approximately 150 $\mu$g of exo-polygalacturonase PGX, purified as described in Example 1.1, was extensively dialysed against distilled water, lyophylized and dissolved in 100 $\mu$l 70% (v/v) formic acid-water mixture. To this protein solution 500 $\mu$g cyanogen bromide (2500 molar excess), dissolved in the formic acid-water mixture, was added. The reaction was performed for 24 hours at room temperature after which the reaction mixture was diluted 10 fold with water following lyophylization.

Approximately one half of the reaction mixture was subjected to electrophoresis on a 15% polyacrylamide gel, followed by blotting onto Immobilon-P membrane (Millipore) according to the method described by Matsudaira (1987). Membrane slices containing fragments with a molecular mass of 30 kD (CB 1), 27.5 kD (CB 2) and 23.5 kD (CB 3) respectively were used in gas-phase sequencing (Applied Biosystems model 470A protein sequencing, SON, Leiden) according to the program described by Amons (1987).

The following N-terminal amino acid sequences were determined:

CB 1 (L2278):
1                5                          10
Ala—(Arg)—Ile—Lys—Val—(Trp)—Pro—Gly—Thr—Pro—Ser—Ala—(Leu)—?—(Ala)
(Formula 1) = (SEQ ID NO: 1)

CB 2 (L1742):
1                5                    10                          15                         20
(Gly)—Ile—Ile—Gly—Leu—Asn—Gly—Gly—Thr—Ile—Gly—Pro—Leu—Lys—Leu—(Arg)—Tyr—Ser—Pro—Gln
(Formula 2) = (SEQ ID NO: 2)

CB 3 (L1743):
1              5                       10
Phe—Ser—(Leu)—Ser—?—Glu—Ala—Ala—(Thr)—Gly—Pro—Lys—Lys—(Pro)—Phe—?—? Leu—(Leu)
(Formula 3) = (SEQ ID NO: 3)

Example 2

Screening of the genomic library of *Aspergillus niger* DS16813 (CBS 323.90; later classified as *A. tubigensis*) for the exo-polygalacturonase gene (pgaX) and isolation of the gene

Example 2.1

Synthesis of a pgaX specific PCR fragment using oligonucleotide mixes derived from PGX amino acid sequences.

The amino acid sequences determined in Example 1.2 (Formulas 1, 2 and 3) were used to synthesize oligonucleotide mixes corresponding to the coding and the non-coding DNA strands. The oligonucleotides are synthesized by the phosphoramidite method, using an Applied Biosystems oligonucleotide synthesizer.

The oligonucleotide mixes (FIG. 1) were used in PCR with chromosomal DNA of *A. tubigensis* NW756 as template. All possible combinations of two oligonucleotide mixtures (100 pmole each) were used in reactions also containing 0.5 µg chromosomal *A. tubigensis* NW756 DNA, 200 µm dNTPs, Taq buffer (Sphaero-Q) and 0.5 U Taq polymerase (Supertaq, Sphaero-Q). Conditions for PCR were 25 cycles of melting at 94° C. (1 minute), annealing at 40° C. (1 minute) and polymerization at 72° C. (2 minutes).

The reaction products were analyzed by electrophoresis using a 2% TAE-agarose gel. Only the combination of oligonucleotide mixture 3059 and 3062 resulted in a reaction product, which was approximately 600 bp in length. This PCR fragment was purified using a the Magic PCR Preps DNA purification system (Promega) following the instructions of the manufacturer.

Example 2.2

$^{32}$P Labelling of DNA Fragments

After purification, the DNA concentration of the PCR fragment described in Example 2.1 was determined. 50 ng was labelled by random priming using the Prime-a-Gene kit from Promega. To remove the unincorporated α-32P-dATP from the mixture, the volume was increased to 100 µl with TE buffer, after which the unincorporated α-32P-dATP was removed by fractionation on a Sephadex G50 column. Fractions containing the radioactively labelled DNA were denatured by incubation for three minutes at 100° C., and kept single stranded by rapidly chilling on ice, before addition to a hybridization buffer containing 6×SSC, 5×Denhardt's solution, 0.1% sodium pyrophosphate and 100 µg/ml heat-denatured herring sperm DNA.

This probe was used in the screening of the genomic library (Example 2.3) and in Southern blot analysis (Examples 2.4, 2.5 and 5.1).

Example 2.3

Screening of the *Aspergillus tubigensis* genomic library for the pgaX gene

To screen for the pgaX gene in an *Aspergillus tubigensis* genomic library, constructed as described in case EP 0 463 706 A1, Example 2, 5.10$^3$ pfu per plate were plated in LM top agarose containing 0.7% agarose on 8 85 mm diameter LM (1.2% agar) plates as described (Maniatis et al., 1982, pp. 64). *E. coli* LE392 were used as plating bacteria.

After incubation of the plates overnight at 37° C., two replicas of each plate were made on nitrocellulose filters (Schleicher and Schüll BA85) as described in Maniatis et al. (1982, pp. 320–321).

After baking the filters for 2 hours at 80° C., the filters were prehybridized at 65° C. for two hours in a prehybridization buffer containing 6×SSC, 0.5% SDS, 10×Denhardt's solution and 100 µg/ml heat denatured herring sperm DNA (Boehringer). The heat-denatured probe was added and the filters were hybridized for 18 hours at 65° C.

After hybridization, the filters were first washed in 2×SSC, 0.5% SDS, and then in 0.2×SSC, 0.5% SDS at 65° C. The air dried filters were taped onto a sheet of Whatman 3MM paper, keying marks were made with radioactive ink and the Whatman paper and filters were covered with Saran Wrap™. Hybridizing plaques were identified by exposure of Kodak XAR X-ray film for 18 hours at −70° C. using an intensifying screen.

Twelve plaques hybridizing with the PCR probe, appearing in duplicate on the replica filters, were identified: $\lambda_{pga}1$ to $\lambda_{pga}12$. Each positive plaque was removed from the plate using a Pasteur pipette and the phages were eluted from the agar plug in 1 ml of SM buffer containing 20 µl chloroform, as described in Maniatis et al. (1982, pp. 64). The phages obtained were purified by repeating the procedure described above using filter replicas from plates containing 50–100 plaques of the isolated phages.

After purification, the phages were propagated by plating 5×10$^3$ phages on LM medium. After incubation overnight at 37° C., confluent plates were obtained, from which the phages were eluted by adding 5 ml SM buffer and storing the plate for 4 hours at 4° C. with intermittent shaking. After collection of the supernatant, the bacteria are removed from the solution by centrifugation at 4,000×g for 10 minutes at 4° C. Chloroform (0.3%) was added to the supernatant and the number of pfu was determined. These phage stocks contained approximately 10$^{10}$ pfu/ml.

Example 2.4

Isolation of DNA from Bacteriophage Lambda

Eight of the isolated phages $\lambda_{pgaX}$ 1, 2, 4, 5, 6, 7, 8 and 11 were propagated as described in Example 2.2 using five plates for each of the phages. The phages were precipitated from the thus-obtained supernatant (25 ml) by addition of an equal volume of a solution containing 20% PEG-6000 (w/v) and 2M NaCl, followed by thorough mixing and incubation on ice for 60 minutes.

The precipitated phages were collected by centrifugation at 14,000×g at 4° C. for 20 minutes. The supernatant was removed by aspiration. The phages were carefully resuspended in 4 ml SM buffer and extracted once with chloroform.

Prior to extracting the DNA from the phage particles, DNA and RNA originating from the lysed bacteria were removed by incubation of the phage suspension with DNase I and RNase A (both 100 µg/ml) for 30 minutes at 37° C. The phage DNA was subsequently released from the phages by extraction with an equal volume of phenol/chloroform (1:1). After separation of the phases by centrifugation using a Sorvall centrifuge (14,000×g, 10 minutes), the aqueous phase was extracted once with an equal volume chloroform. The phases were separated by centrifugation (Sorvall centrifuge, 14,000×g, 10 minutes) after which the DNA was precipitated from the aqueous phase by the addition of 0.1 volume 3M sodiumacetate and 2 volumes ethanol. After mixing, the DNA was recovered by centrifugation in a Sorvall centrifuge for 10 minutes at 4° C. (14,000×g).

The supernatant was removed by aspiration after which the DNA was resuspended in 400 µl TE buffer. The DNA was precipitated once again from this solution by the addition of 0.1 volume 3M sodium acetate and 2 volumes ethanol. The DNA was collected by centrifugation for 10 minutes at 4° C. (14,000×g). The supernatant was removed by aspiration, the remaining pellet was briefly dried under vacuum, after which the DNA was resuspended in 125 µl TE buffer containing 0.1 µg/ml RNase A. This purification procedure resulted in the isolation of approximately 10–50 µg DNA from each phage.

Example 2.5

Restriction Analysis of pgaX Containing Phages

The isolated DNA of phages $\lambda_{pgaX}$ 1, 2, 4, 5, 6, 7, 8 and 11 was analyzed by Southern analysis using the following restriction enzymes: PvuII and HincII. The DNA was digested for 3 hours at 37° C. in a reaction mixture composed of the following solutions; 3 µl (≈1 µg) DNA solution; 10 µl of the appropriate 10×React buffer (BRL); 20 U restriction enzyme (BRL) and sterile distilled water to give a final volume of 100 µl.

After digestion the DNA was precipitated by the addition of 0.1 volume 3M NaAc and 2 volumes ethanol. The DNA was collected by centrifugation for 10 minutes at room temperature (14,000×g). The supernatant was removed by aspiration, the remaining pellet was briefly dried under vacuum and resuspended in sterile distilled water.

After addition of 4 µl DNA loading buffer the samples were incubated for 10 minutes at 65° C. and rapidly cooled on ice. Samples were loaded on a 6.0% agarose gel in TAE buffer. The DNA fragments were separated by electrophoresis at 25 V for 15–18 hours.

After electrophoresis the DNA was transferred to nylon membrane (Gene Bind 45, Pharmacia LKB) by Southern blotting as described in Maniatis et al. (1982) and subsequently prehybridized and hybridized using the labeled PCR fragment as described in Example 2.1 and hybridization conditions as described in Example 2.2. The hybridization pattern was obtained by exposure of Kodak XAR-5 X-ray film for 18 hours at −70° C. using an intensifying screen.

From the results obtained it was concluded that the DNA of all isolated clones hybridize with the PCR fragment. Two clones appeared to be identical and contained a very large hybridizing PvuII fragment. No hybridizing HincII fragment was detected, suggesting that this fragment was too small and had run off the gel. In six clones fragments originating from the same genomic region were found. In a more extensive Southern analysis, using the enzymes XhoI, PvuII, PstI, BglII, SalI, EcoRI and BamHI a partial restriction map of this genomic region was constructed. From this experiment it was concluded that a 5.8 kb XhoI fragment contains the A. tubigensis pgaX gene.

Example 2.6

Subcloning of the A tubigensis pgaX Gene

From phage $\lambda_{pgaX}$7 the 5.8 kb XhoI fragment was isolated by digesting the phage DNA with XhoI and separation of the fragments as described in Example 2.4. The fragment was cut from the agarose gel, after which it was recovered from the agarose using GeneClean (Bio101) as described by the manufacturer. The DNA was dissolved in 10 µl sterile water and the concentration was determined by agarose electrophoresis, using lambda DNA with a known concentration as a reference and ethidiumbromide staining to detect the DNA.

The fragment obtained was ligated in the vector pEMBL19 digested with SalI and dephosphorylated with alkaline phosphatase prepared as follows; 1 µl (1 µg/µl) pEMBL19 was mixed with 2 µl 10×React 10 (BRL), 1 µl (1 U/µl) SalI and 16 µl sterile distilled water. The DNA was digested for 1 hour at 37° C., after which 0.5 µl alkaline phosphatase (1 U/µl) Pharmacia LKB) was added followed by further incubation at 37° C. for another 10 minutes.

The 5.8 kb XhoI fragment was ligated in the vector resulting in the plasmid pIM362, by the following procedure: 100 ng pEMBL19 fragment was mixed with 100 ng 5.8 kb XhoI fragment and 4 µl 5*ligation buffer (BRL) and 1 µl (1.2 U/µl) DNA ligase (BRL) was added to this mixture in a final volume of 20 µl. After incubation for 16 hours at 4° C., 10 µl of the mixture was used to transform E. coli JM101 competent cells, prepared by the CM1, CM2 method as described in the Pharmacia Manual for the M13 cloning/sequencing system. One of the resulting colonies was grown overnight in LB medium containing 100 µg/ml ampicillin. From the culture plasmid DNA was isolated by the alkaline lysis method as described by Maniatis et al. (1982, pp., 368–369), which was used in restriction analysis, as described in Example 2.4 to check whether it harboured the desired plasmid. Plasmid DNA was isolated on a large scale from 500 ml cultures E. coli JM101 containing the plasmid pIM362 grown in LB medium containing 100 µg/ml ampicillin (Maniatis et al., 1982, p.86) The plasmid was purified by CsCl density gradient centrifugation, phenolized, ethanol precipitated and dissolved in 400 µl TE. The yield was approximately 500 µg.

Similarly, a 4.0 kb PvuII fragment which is located within the 5.8 kb XhoI fragment, was isolated from phage 7, subcloned in pEMBL19 digested with SmaI, resulting in plasmid pIM361.

The plasmid pIM361 was further analyzed by restriction enzymes resulting in the restriction map shown in FIG. 2.

Plasmids pIM361 and pIM362 containing the exo-PG gene have been deposited in E. coli JM101 at the Centraal Bureau voor de Schimmelcultures in Baarn, The Netherlands and have received the deposition number CBS 101.93 and CBS 102.93, respectively.

Pursuant to the applicable requirements of U.S. patent law, as of the issuing of U.S. Pat. No. 5,624,834 on Apr. 29, 1997, all restrictions imposed on the availability to the public of these deposited materials were irrevocably removed.

Example 3

Characterization of the *Aspergillus tubigensis* pgaX Gene

Example 3.1

Sequence Determination of the *A. tubigensis* pgaX Gene

The sequence of the *A. tubigensis* pgaX gene was determined by subcloning fragments from pIM362 in pEMBL18/19, in combination with the use of specific oligonucleotides as primers in the sequencing reactions.

For nucleotide sequence analysis restriction fragments were isolated as described in Example 2.5 and then cloned in pEMBL18/19 vectors digested with the appropriate restriction enzymes, as described in Example 2.5. The nucleotide sequences were determined by the dideoxynucleotide chain-termination procedure (Sanger et al., 1977) using the Pharmacia $T_7$ DNA polymerase sequencing kit. Computer analysis was done using the PC/GENE program (Intelligenetics, Inc.: Madison, Wis.). The sequence was determined for 98% in both orientations Sequence Listing). The sequence includes about 640 pb of the 5' and 655 bp of the 3' sequence.

Example 3.2

The *A. tubigensis* pgaX Gene Structure

There are probably 6 introns present in the gene. This is based on the appearance of in frame stopcodons in all of the introns and on the presence of intron consensus sequences (Table II).

TABLE II

Intron sequences of the pgaX gene.

| | position | length | 5' site | lariat | 3' site |
|---|---|---|---|---|---|
| Intron I | 948–1004 | 57 | GTGctT | ACTAAC | CAG |
| Intron II | 1372–1423 | 52 | GTGcGT | ACTGAC | TAG |
| Intron III | 1483–1540 | 58 | GTAaGT | tCTAAC | CAG |
| Intron IV | 1942–1991 | 50 | GTtaGT | GCTAtC | TAG |
| Intron V | 2094–2145 | 52 | GTAaGT | gCTGAC | TAG |
| Intron VI | 2221–2273 | 53 | GTGaGT | ACTAAC | CAG |
| consensus | | | GTPuNGT | PuCTPuAC | PyAG |

The pgaX gene encodes a secreted protein of 47.1 kD and an iso-electric point of 4.11. The calculated molecular weight is lower than the one determined by SDS-PAGE (78 kD), even after deglycosylation (52 kD) (there are 12 possible N-glycosylation sites in PGX). Discrepancies between calculated and determined molecular weights have also been found for other proteins. All three CNBr fragments are found in the sequence. L1743 appears to represent the N-terminal amino acid sequence of the mature exo-PG protein: no methionine is found immediately preceding the phenylalanine (F), which would have been expected if it were a true CNBr fragment. Instead a sequence with the characteristics of a signal sequence is found. According to the computer program PC-GENE the preferred signal sequence splice site is between serine (S 24) and arginine (R 26), however, since these amino acids are found in the mature protein, this is not the case. The splice site between the alanine (A 22) and phenylalanine (F 23) is second best.

Example 4

Expression of the pgaX gene in *Aspergillus niger* N593, *Aspergillus tubigensis* NW218 and *Aspergillus nidulans* G191

Example 4.1

Introduction of the pgaX gene into *Aspergillus niger* N593, *Aspergillus tubigensis* NW218 and *Aspergillus nidulans* G191 by cotransformation The plasmids pIM361 and pIM362, obtained in Example 2.5, were introduced in *A. niger*, *A. tubigensis* and *A. nidulans* by cotransformation of *A. niger* N593, *A. tubigensis* NW218 and *A. nidulans* G191 using the *A. niger* pyrA gene as a selective marker on the plasmid pGW635 (goosen et al., 1989) and the plasmids pIM361 and pIM362 as the cotransforming plasmids in separate experiments.

Protoplasts were prepared from mycelium by growing *A. niger* N593 and *A. tubigensis* NW218 on minimal medium supplemented with 0.5% yeast extract, 0.2% casamino acids, 50 mM glucose and 10 mM uridine for 20 hours at 30° C. For the preparation of protoplasts *A. nidulans* G191 was grown at 37° C. on the same medium supplemented with 1.35 mg/l p-aminobenzoate. The preparation of protoplasts and the transformation procedures were performed as described by Goosen et al., 1987. The resulting $pyr^+$ transformants were then analyzed for the expression of the pgaX gene by Western blot analysis.

Example 4.2

Screening of transformants for the expression of the pgaX gene

The transformants obtained in Example 4.1 were analyzed for the formation of the pgaX gene product, the PGX protein. 10 pIM361 and 10 pIM362 *A. niger* transformants, 5 pIM361 and 5 pIM362 *A. tubigensis* transformants and 10 pIM361 and 10 pIM362 *A. nidulans* transformants were selected and grown for 24 hours on medium containing per liter 10 g PGII-degraded polygalacturonic acid, 7.5 g $NH_4NO_3$, 0.5 g KCl, 0.5 g $MgSO4.7H_2O$, 1.5 g $KH2PO_4$, 0.2% yeast extract, 1 ml/l Vishniac solution and 1.35 mg/l p-aminobenzoate for *A. nidulans* only (pH 6.0).

After growth (24 hours after inoculation) the mycelium was removed by filtration and the proteins in the culture filtrates were analyzed by the SDS-polyacrylamide gel electrophoresis, using a gel containing 10% acrylamide.

The PGX protein was detected on nitrocellulose after electroblotting and incubation with polyclonal antibodies raised against the PGX protein purified as described in Example 1.1. The antibody bound, was detected after incubation with goat-anti-mouse antibody conjugated to alkaline phosphatase, according to the Biorad instruction manual.

TABLE III

Transformants which overproduce PGX.

| | | t = 24 |
|---|---|---|
| *A. tubigensis* | (pIM361)4 | ++ |
| | (pIM361)6 | +++ |
| | (pIM362)7 | + |
| *A. nidulans* | (pIM361)6 | ++ |
| | (pIM361)9 | +++ |
| | (pIM362)2 | ++ |

The amount of PGX produced as judged by Western analysis is indicated.
+++: high overproduction as compared to the corresponding wild type strain.
+: low overproduction as compared to the corresponding wild type strain.

Table III shows the results of the Western analysis. Only *A. tubigensis* and *A. nidulans* transformants readily overproduced the PGX protein as detected by this procedure. The protein was secreted into the medium. Of the *A. tubigensis* transformants analyzed one was selected for giving the highest yields of the PGX protein, transformant *A. tubigensis* NW218(pIM361)6.

In a second experiment *A. tubigensis* NW218 was transformed with 1 μg of pGS613 which contains the *A. niger* pyrA gene and 40 μg pIM361. The highest producer found in this experiment was NW218 (pIM361)22.

Example 4.3
Overexpression of PGX in *A. tubigensis* transformants and purification and characterization of PGX PGX was purified from *A. tubigensis* NW756. NW756 was grown for 48 h at 30° C. in medium containing 7.5 g ammonium nitrate. 1.5 g $KH_2PO_4$, 0.5 g KCl, 0.5 g $MgSO_4.7H_2O$, 2 g yeast extract, tract elements and 1% PGII-degraded polygalacturonic acid, pH 6.0. The culture fluid was harvested by filtration and the pH (initial value 6.8) was adjusted to 6.0. The culture filtrate was stirred for one hour with DEAE-Sephadex A50 (300 g, wet weight), equilibrated in 10 mM sodium phosphate buffer pH 6.0. The ion-exchanger was collected, poured into a column, and bound protein was eluted by a pulse of 1M NaCl in buffer. After dialysis against 20 mM sodium acetate buffer pH 4.2 the solution was loaded on a crosslinked alginate column (0=5 cm, h=8 cm) in the same buffer followed by elution with two pulses of respectively 0.3 and 1M NaCl in buffer. Part of the exo-PG activity did bind to the crosslinking alginate column and was eluted by the 0.3M NaCl pulse (pool I). The non-bound fraction was dialyzed against 20 mM sodium citrate buffer pH 3.5 and loaded on a S-Sepharose Fast Flow column (0=2.5 cm, h=25 cm) equilibrated in the same buffer followed by elution by a 600 ml NaCl gradient (0–0.6M) (pools I, II, III). These pools all contained exo-PG activity and all also contained endo-PG activity except pool I of the S-Sepharose column.

All four pools were concentrated up to 5 ml by adsorption on a small (0=1.5 cm, h=5 cm) DEAE-Sepharose Fast Flow column at pH 6.0 followed by pulse elution with 1M NaCl in 10 mM sodium phosphate buffer pH 6.0. The final purification was done by GPC on a Sephacryl-S 200 column (0=2.5 cm, h=90 cm) in 0.1M sodium acetate buffer pH 4.8.

No endo-PG and PL activity could be detected in these final samples.

|  | volume | U/ml | mg/ml | S.A. |
|---|---|---|---|---|
| crl. gen. pool I/GPC/conc. | 9.8 | 19.4 | 0.54 | 36 |
| S-Seph. pool II/GPC | 22.7 | 1.28 | 0.017 | 75 |
| S-Seph. pool III/GPC/conc. | 6.5 | 14.4 | 0.31 | 46.5 |

S.A. = specific activity

Purification of PGX from transformant NW218 (pIM361) 22.

Cultivation was done for 50 h at 30° C. in minimal medium with ammonium nitrate as nitrogen source and 1% PGII-degraded polygalacturonic acid as carbon source. After 24 and 50 h only one major protein could be detected in the culture fluid as judged by Coomassie Brilliant Blue-staining following SDS-polyacylamide gel electrophoresis. Total protein in the culture filtrate was concentrated by batch wise adsorption on DEAE A50 pH 6.0 followed by pulse elution with 1M NaCl in 20 mM sodium phosphate buffer pH 6.0.

After extensive dialysis against 20 mM sodium acetate buffer pH 3.6 dialysate was loaded onto a S-Sepharose Fast Flow column (2.5*20 cm) equilibrated in the same buffer. Elution was done with a linear NaCl gradient (800 ml, 0–1.5M).

Fractions were screened by SDS-PAGE and based on these results two pools were formed which were used for further analysis.

|  | U/ml | mg/ml | U/mg | mg | total U |
|---|---|---|---|---|---|
| Pool I | 39.5 | 0.87 | 45.4 | 61 | 2.765 |
| Pool II | 400 | 5.1 | 78 | 790 | 12.900 |

Based on these results the production level of PGX in this transformant (approx. 180 mg/l) is 80 fold higher than for the wild type strain NW756.

After one purification step the preparation is not completely pure, but no pectin lyase and no endo-PG activity could be detected. Pool I contains a low level of pectinesterase activity.

Example 4.4
Deregulated expression of the *A. tubigensis* pgaX gene

To make a gene fusion of the *A. niger* N400 pki promoter and the *A. tubigensis* DS16813 pgaX gene, first a PCR fragment was made using a primer which contains the pki SmaI site and another primer containing the *A. niger* pki ATG and the first 12 nucleotides of the pgaX gene (pgaX sequences are shown in small letters):

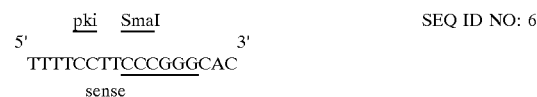

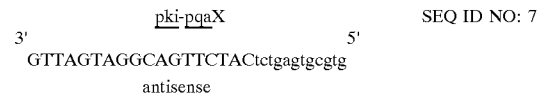

Similarly, a PCR fragment was made using an oligo complementary to the pki-pgaX primer described above and another primer containing a NcoI site 165 bp upstream in the pgaX coding region:

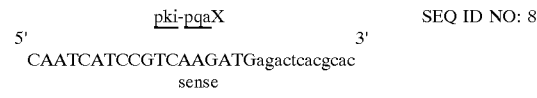

Subsequently, both PCR fragments were used in a third PCR experiment with only the pki SmaI primer and the pgaX NcoI primer. This resulted in a fragment of approx. 300 bp which was digested with SmaI and NcoI to obtain the desired sticky ends and the fragment was then further purified.

pIM361 was digested with BamHI which cuts in the pEMBL polylinker. A BamHI fragment containing the pki promoter and the *A. niger* pe1B gene was cloned into this plasmid. Digestion with NcoI and SmaI cut out the pe1B gene as well as the 5' end of the pgaX gene and the 3' end of the pki promoter. Ligation of the SmaI-NcoI PCR fragment described above resulted in pIM365 which thus contains the *A. niger* pki promoter fused to the *A. tubigensis* pgaX gene. The construct was checked by sequencing, using the commercial universal and reverse primers as well as the pki-SmaI and pgaX-NcoI primers to sequence the PCR fragment.

*A. tubigensis* NW218 was transformed with the *A. niger* pyrA gene (pGW635, 1 μg) and pIM365 (40 μg) as cotransforming plasmid. Only two PGX overproducing transformants have been found, NW218 (pIM365) number 52 and 59, of which 59 has the highest production level. The copynumber of pgaX in this transformant has not yet been established.

Example 5
Screening for genes related to the pgaX gene in *Aspergillus niger, Aspergillus tubigensis* and *Aspergillus nidulans*

Example 5.1
Genomic hybridization of *A. niger, A. tubigensis* and *A. nidulans* DNA High molecular weight DNA isolated from *A. niger* N400, *A. tubigensis* NW756 and *A. nidulans* WE312 as described in the published european patent application EP 0 463 706, Example 2.1, was digested with EcoRI, BamHI and HindIII. The resulting fragments were separated by agarose gel electrophoresis and transferred to nitrocellulose membrane as described by Maniatis et al. (1982, pp. 383–389).

The nitrocellulose membranes were prehybridized at 60° C. for two hours in hybridization buffer (as described in Example 2.2, above). After prehybridization, the radioactively labelled fragment, described in Example 2.2, was added to the hybridization buffer and the hybridization was contained for 18 hours. After hybridization, the filters were washed for 60 minutes at 60° C. in 4×SSC, 0.5% SDS followed by final washing using 2×SSC, 0.5% SDS at 60° C.

After taping the membranes to Whatmann 3MM paper and properly marking with radioactively labelled ink, the filters were covered with Saran Wrap™ and autoradiographed for 72 hours at −70° C. using Kodak XAR-5 X-Ray film and Kodak X-Omatic cassettes with regular intensifying screens.

The hybridization fragments found are summarized in Table IV.

TABLE IV

Hybridizing fragments and their lengths (kb) found in *A. niger, A. tubigensis* and *A. nidulans* genomic DNA using a fragment of the *A. tubigensis* pgaX gene as a probe.

|                    | EcoRI | BamHI | HindIII |
|--------------------|-------|-------|---------|
| *A. niger* N400    | 13    | 9.0   | 2.5     |
|                    |       | 6.0   | 1.9     |
|                    |       | 4.4*  | 1.6*    |
| *A. tubigensis* NW756 | 5.5 | 23$^1$ | 2.5    |
|                    |       | 12$^1$ |         |
|                    |       | 9.0*  |         |
| *A. nidulans* WG312 | 4.4  | 1.3   | 3.4     |

*strongest hybridizing fragment
$^1$partially digested

Example 6
Effect of exo-polygalacturonase on calcium sensitivity and molecular weight of pectin
Methods
Exo-PG and Rohament PL were used in these experiments.

Exo-PG was isolated from the supernatant of an *A. tubigensis* culture. Exo-PG was stored frozen in 20 mM sodium citrate buffer pH 3.5. Exo-PG had an activity of 14.4 U/ml and a concentration of 0.31 mg/ml. No lyase and endo-polygalacturonase activities could be detected in the exo-PG solution. The activity was measured on polygalacturonic acid at a concentration of 0.25% (W/V) in 0.1M sodium acetate pH 4.2 at 30° C.

Rohament PL was obtained from Rohm GmbH (Darmstadt, Germany). The activity was 2500 pgu/ml measured according to internal Rohm standards.

Pectin used for the test system has the following characteristics:
degree of ester=71.7 (by titrimetry),
molecular weight=117 kD, as described below,
calcium sensitivity=213, according to the test described below.

Molecular Weight Determination for Pectin
Principle
Molecular weight is estimated by measuring the relative viscosity of a 0.1% pectin solution using Na-hexametaphosphate.
Apparatus
1. Ostwald capillary tube viscosimeters (no less than two) with 100 to 150 sec. outlet time for water (25° C.). For instance Silber Brand #111.
2. Transparent thermostated water bath, 25.0° C.±0.3° C.
Reagents
1. Na-hexametaphosphate solution:
a) 20.0 g Na-hexametaphosphate is dissolved in 1800 ml ion exchanged deaerated (boiled) water.
b) pH is adjusted to 4.50±0.05 with 1M HCl.
c) The solution is diluted with ion exchanged, deaerated (boiled) water until 2000 ml.
Procedure
1. The viscosimeters must be cleaned appropriately.
2. Outlet time for hexametaphosphate solution is measured (section: Measuring of outlet time) on the viscosimeters used every time a new hexameta-phosphate solution is prepared and for every new working day where pectin solutions are being measured.
Immediately before measuring the necessary quantity of hexametaphosphate solution is filtered through a glass filter #3.
3. The pectin sample system for molecular weight determination is made as follows:
a) Acid wash the pectin as described in the method for determination of AGA and DE (Food Chemicals Codex, 3rd Edition, Washington, D.C., 1981).
b) Approx. 90 g hexametaphosphate solution is weighed in a tared beaker with magnet.
c) 0.1000 g acid washed pectin is gradually added while stirring. Keep stirring until the pectin is completely dissolved.
d) Weight up to 100.0 g with hexametaphosphate solution.
e) Filter through a glass filter×3.
4. For every molecular weight determination the outlet time is measured (section: Measuring the outlet time) for the pectin/hexametaphosphate solution on two different viscosimeters.
5. Molecular weight is calculated (section: Calculation) separately for each viscosimeter using the latest measured outlet time for hexametaphosphate solution on the viscosimeter in question.
6. Should the difference between two calculated molecular weights be less than 3500 the mean value is calculated. Round off the value to the nearest multiple of 1000 and that will be the result of the method.
7. should the difference between the two calculated molecular weights be 3500 or more the viscosimeters should be cleaned and a new measuring of outlet time for hexametaphosphate solution should be performed.
Measuring the Outlet Time
1. The viscosimeter is rinsed twice with the sample.
2. Pour 5.00 ml of the sample in the viscosimeter and place it in the thermostated water bath at 25.0° C.±0.3° C. at least 15 minutes prior to measuring.

3. Time is measured on two outlets. Should the difference between the times be more than x seconds the measuring is repeated until you have three outlet times which differ no more than x seconds.

x=0.2 seconds on measuring hexametaphosphate solution
x=0.4 seconds on measuring samples 4. The outlet time which is needed for further calculations is the mean value of the above mentioned two or three identical or almost identical measuring results.

Calculation

The relative viscosity is calculated, as follows:

$$n_r = \frac{\left(t_o - \frac{K}{t_o}\right)}{\left(t_h - \frac{K}{t_h}\right)}$$

Where $t_o$ and $t_h$ are outlet times for pectin solution and hexametaphosphate solution, respectively.

The parameter K can with sufficient accuracy be fixed at 75 $s^2$ using Silber Brand No. 111 viscosimeter. Otherwise, K can be calculated as follows:

$$K = \frac{Q \times t_v^2}{Q + (0.226 \cdot L \cdot t_v)}$$

where Q=volume of viscosimeter bulb in $cm^3$, L=length of capillary tube in cm and $t_v$ outlet time for water in seconds. The molecular weight of pectin is calculated as follows:

$$M = \frac{(n_r^{1/P} - 1) \cdot P}{k \cdot C}$$

where P is fixed at 6 and k is fixed at $4.7 \cdot 10^{-5}$ mol·$g^{-1}$; c is the weight percentage of pectin in the sample system—i.e. 0.1% with the numerical values inserted you will obtain:

$M = 1.277 \cdot 10^6 (n_r^{1/6} - 1) g/mol$.

Literature

P. E Christensen (1954) and Smit and Bryant (1967)

Calcium Sensitivity Test

A calcium containing pectin solution is prepared under conditions avoiding the formation of local gels during the addition of the calcium salt to the pectin solution.

The calcium salt and pectin are mixed at low pH prohibiting the reaction between calcium and pectin. This reaction is initiated by increasing the pH by adding an acetate buffer to obtain the desired pH.

Reagents:

1M Hcl

1M Acetate buffer, pH 4.75

250 mM Calcium chloride solution

A pectin solution of the desired concentration is prepared in distilled water, and pH adjusted to 1.5 with 1M HCl.

145 g portions of this pectin solution are measured into viscosity glasses.

5 ml of the calcium chloride solution is added to the 145 g pectin solution to give a final concentration of 8.3 mM Ca.

With efficient stirring with a magnetic stirrer, 25 ml of the acetate buffer is added to the pectin solution to bring pH to 4.2.

The magnet is taken out, and the glass is left at room temperature (25° C.) until the next day, when the viscosity is measured with a Brookfield viscosimeter. The pectin used in the present experiments had calcium sensitivity=213, according to this test.

Test for Polygalacturonase Activity

Two enzymes are tested in every experiment: exo-PG and Rohament PL.

(1) A 1.6% pectin solution is prepared, and pH is adjusted to 3.8 with dilute $NH_3$ solution or dilute HCl. The solution is kept at 38° C.

(2) Three dilutions of each enzyme (in 20 mM sodium citrate buffer, pH 3.5) are prepared. The concentrations are chosen in accordance with the expected activity of the enzymes so a considerable (but not exhaustive) reduction of the calcium sensitivity of the pectin is achieved when the test system is incubated with the enzyme dilutions as will be detailed in the following text. Further, the concentrations of the three dilutions are in the relative proportions 1:2:4.

(3) The pectin solution is split in nine portions, 95 g each. Three of these are incubated with 5 ml of each dilution of the "unknown" enzyme. Three portions are incubated with the "standard" enzyme. The remaining three portions are incubated with 5 ml water, they are referred to as "blanks".

(4) All nine test systems are treated in the same way:
   (a) incubation at 38° C. for 20 hours
   (b) addition of 100 ml diluted HCl, the concentration is chosen by experience so that the pH of the test system becomes 1.8±0.2
   (c) heating on water bath for 4 minutes at 85° C., measured from the time when 70° C. was reached (this treatment should destroy the enzyme)
   (d) cooling to 25° C. on water bath.

(5) Each of the so treated pectin solutions is split into two portions: one of these is made into—and measured as—a test system for pectin molecular weight, while the other is made into a test system for calcium sensitivity.

The test system for molecular weight is 0.1% pectin in sodium hexametaphosphate solution, pH 4.5. The viscosity is measured in an Ostwald capillary and converted to (what is reported as) molecular weight by a numerical expression. Details are given above The test system for calcium sensitivity is 0.6% pectin in sodium acetate buffer with added $Ca^{++}$, pH 4.4. The viscosity is measured by means of a Brookfield viscosimeter. Details may be found above.

Results

The results are reported in a diagram with MW-change (in kD, relative to the average of the blanks) as the x-axis and calcium sensitivity (in cp) as the y-axis. An enzyme showing desired performance, i.e. a low calcium sensitivity is achieved with almost no loss in molecular weight, will have data points in the lower right corner of the diagram.

Figure 3:
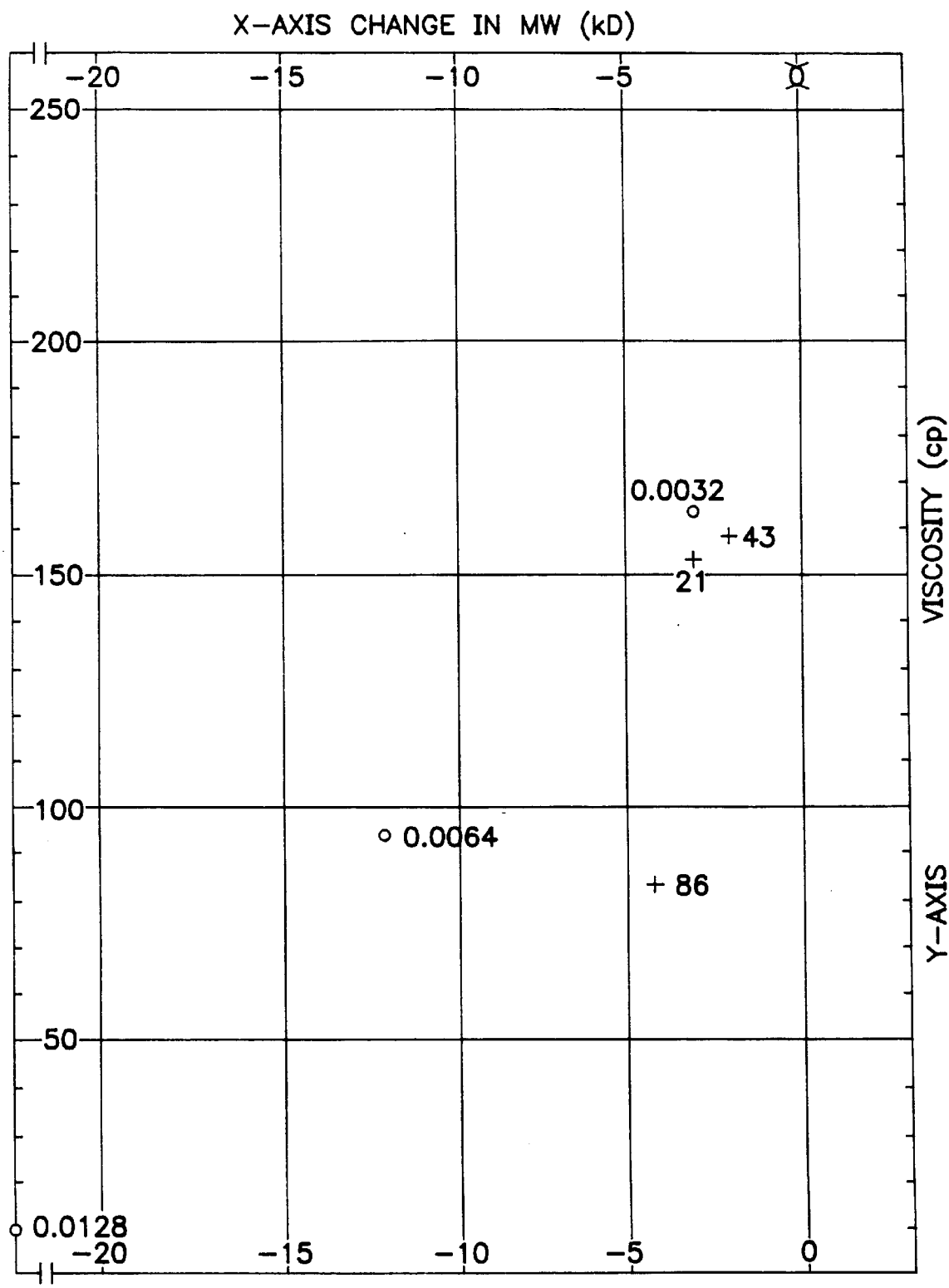
FIGS. 3 and 4 show the results of the use of exo-PG versus Rohament PL for reducing the calcium sensitivity of pectin. X-axis shows molecular weight change (in kD) and Y-axis shows viscosity (in centipoise). The dosages of enzyme in mg per g pectin are printed next to the data points.
Figure 4:
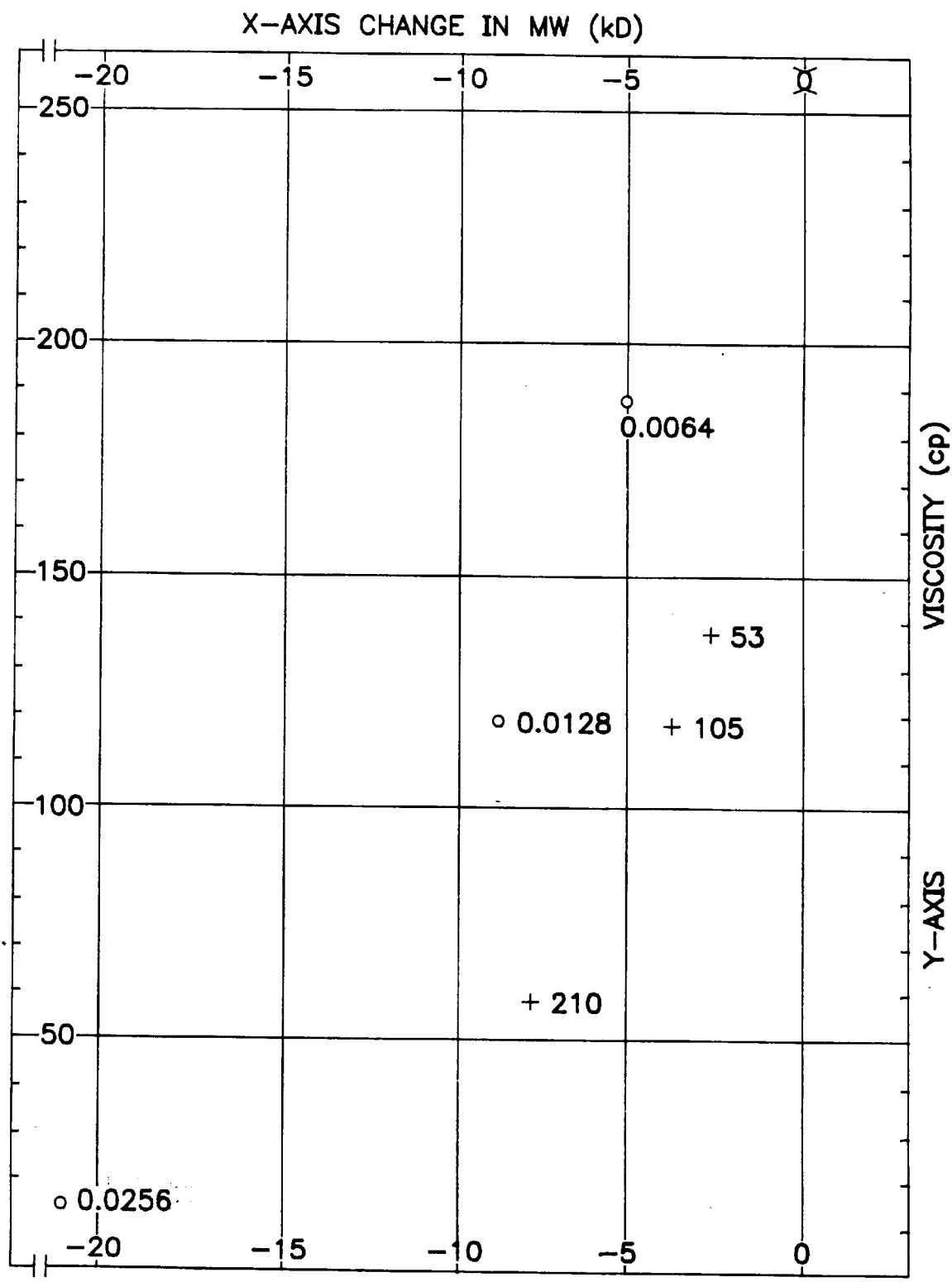

Results of the two independent experiments are shown as FIGS. 3 and 4. The dosages of enzyme in mg per g pectin are printed next to the data points.

The Figures presented lead to the conclusion that:

(1) The exo-PG preparations can reduce the calcium sensitivity of the pectin that was used in the test system.

(2) In both experiments, data points for the exo-PGs tend to be to the lower right side of the data points for the standard (Rohament PL) in the diagrams, FIGS. 3 and 4. This suggests that for this particular purpose an exo-PG is more desirable in its way of action than Rohament PL.

The above data suggest that a great part of the calcium sensitivity of pectin is due to blocks situated at the non-reducing ends of some of the pectin molecules.

REFERENCES

Amons, R. (1987) FEBS Lett. 212: 68–72.

Christenses, P. E. (1954) Food Research 19: 163–171.

Dente, L., Cesari, G. and Cortese, R. (1983) Nucl. Acids Res. 11: 1145–1655.

Goosen, T., Bloemheuvel, G., Gysler, C., de Bie, D. A., van den Broek, H. W. J. and Swart, K. (1987), Curr. Genet. 11: 499–503.

Goosen, T., van Engelenburg, F., Debets, F., Swart, K., Bos, K. and van den Broek, H. W. J. (1989) Mol. Gen. Genet. 219: 282–288.

Kester, H. C. M. and Visser, J. (1990) Biotech. Appl. Biochem. 12: 150–160.

Kusters-van Someren, M. A., Samson, R. A. and Visser, J. (1991) Curr. Genet. 19: 21–26.

Maniatis, T., Fritsch, E. F. and Sambrook, J. (1982) Molecular cloning, a laboratory manual; Cold Spring Harbor Laboratory, New York.

Matsudaira, P. (1987), J. Biol. Chem., 262: 10035–10038.

Murray, N. (1977) Mol. Gen. Genet. 150: 53–58.

Snager, F., Nickelen, S. and Coulson, A. R. (1977), Proc. Natl. Acad. Sci. USA 74: 5463–5467.

Smit, C. J. B. and E. F. Bryant (1967), J. of Food Science 32: 197–199.

Stephens, B. G., Felkel, H. J. Jr. and Spinelli, W. M. (1974) Anal. Chem. 46: 692–696.

Vischniac, W. and Santer, M. (1957), Bact. Rev. 21: 195–213.

Yanisch-Perron, C., Vieira, J. and Messing, J. (1985) Gene 33: 103–109.

---

We claim:

1. A purified and isolated polynucleotide molecule which encodes a polypeptide having the activity of an exo-polygalacturonase enzyme, which comprises a nucleotide sequence selected from the group consisting of:
   (a) a nucleotide sequence that encodes an exo-polygalacturonase enzyme having the amino acid sequence depicted in SEQ ID NO: 5; and
   (b) a nucleotide sequence that encodes a polypeptide having exo-polygalacturonase activity, wherein said nucleotide sequence hybridizes to a sequence (a), or a fragment thereof, in 6×SSC at 60° C. or conditions equivalent thereto.

2. A polynucleotide molecule according to claim 1, wherein the encoding sequence thereof is operably linked to one or more expression regulatory sequences capable of directing expression therefrom in a host cell.

3. A vector containing a polynucleotide molecule according to claim 2.

4. A microbial host cell capable of expressing a gene encoding a protein having exo-polygalacturonase activity, wherein said host cell has been altered to contain a vector according to claim 3.

5. A method for obtaining expression of exo-polygalacturonase that comprises culturing a microbial host cell of claim 4 under conditions wherein the cloned gene therein is expressed.

6. A method for obtaining exo-polygalacturonase comprising the steps of:
   (a) culturing a microbial host cell of claim 4 under conditions giving rise to the expression of the DNA sequence that encodes said exo-polygalacturonase; and
   (b) recovering the polypeptide having exo-polygalacturonase activity.

7. A purified and isolated polynucleotide molecule that encodes an Aspergillus exo-polygalacturonase enzyme, which comprises a nucleotide sequence selected from the group consisting of:
   (a) a nucleotide sequence that encodes an exo-polygalacturonase enzyme having the amino acid sequence depicted in SEQ ID NO: 5; and
   (b) a nucleotide sequence which hybridizes to a sequence (a), or a fragment thereof, in 6×SSC or conditions equivalent thereto.

8. A composition comprising nucleic acid molecules that contain an encoding sequence for an enzyme having exo-polygalacturonase activity, which composition is substantially free of nucleic acid molecules not containing said encoding sequence, wherein said sequence is selected from the group consisting of:
   (a) SEQ ID NO: 4;
   (b) a nucleotide sequence complementary to (a);
   (c) a nucleotide sequence that encodes an enzyme having exo-polygalacturonase activity, wherein said enzyme is encoded by one or more nucleotide sequences which will selectively hybridize with (a) or (b) in 6×SSC at 60° C., or conditions equivalent thereto; and
   (d) a nucleotide sequence which encodes an enzyme having exo-polygalacturonase activity, wherein a fragment of said encoding nucleotide sequence hybridizes to sequence (a) or (b) in 6×SSC at 60° C., or conditions equivalent thereto.

9. A polynucleotide molecule comprising an encoding sequence for an enzyme having exo-polygalacturonase activity that is selected from the group consisting of:
   (a) SEQ ID NO: 4;
   (b) a nucleotide sequence complementary to (a);
   (c) a nucleotide sequence that encodes an enzyme having exo-polygalacturonase activity, which enzyme is encoded by one or more nucleotide sequences that will selectively hybridize with (a) or (b) in 6×SSC at 60° C., or conditions equivalent thereto; and
   (d) a nucleotide sequence which encodes an enzyme having exo-polygalacturonase activity, wherein a fragment of said encoding nucleotide sequence hybridizes to sequence (a) or (b) in 6×SSC at 60° C., or conditions equivalent thereto
wherein said encoding sequence is operably linked to an expression regulatory sequence capable of directing the expression of said polynucleotide molecule in a suitable host organism.

10. A vector containing the polynucleotide molecule of claim 9.

11. A microbial host cell capable of expressing a gene encoding a protein having exo-polygalacturonase activity wherein said host cell has been altered to contain a vector of claim 10.

12. A method for obtaining expression of a protein having exo-polygalacturonase activity comprising, culturing the microbial host cell of claim 11 under conditions wherein the cloned gene is expressed.

13. A method of obtaining an enzyme having exo-polygalacturonase activity comprising the steps of:
   (a) culturing the microbial host cell of claim 11 under conditions giving rise to the expression of the encoding sequence for exo-polygalacturonase therein, and
   (b) recovering the polypeptide having exo-polygalacturonase activity.

14. A purified and isolated polynucleotide molecule which encodes a polypeptide having the activity of the Aspergillus

*tubigensis* exo-polygalacturonase enzyme, which comprises a nucleotide sequence selected from the group consisting of:

(a) a nucleotide sequence that encodes an enzyme having exo-polygalacturonase activity, and having the amino acid sequence depicted in SEQ ID NO: 5; and (b) a nucleotide sequence which encodes an enzyme having exo-polygalacturonase activity, wherein said nucleotide sequence hybridizes to a sequence (a), or to a fragment thereof, in 6×SSC at 60° C. or conditions equivalent thereto.

15. The polynucleotide molecule of claim 14, wherein said polynucleotide molecule is operably linked to an expression regulatory sequence capable of directing the expression of said polynucleotide molecule in a suitable host organism.

16. A vector containing the polynucleotide molecule of claim 15.

17. A microbial host cell capable of expressing a gene encoding a protein having exo-polygalacturonase activity wherein said host cell has been altered to contain a vector of claim 16.

18. A method for obtaining expression of a protein having exo-polygalacturonase activity comprising, culturing the microbial host cell of claim 17 under conditions wherein the cloned gene is expressed.

19. A method of obtaining an enzyme having exo-polygalacturonase activity comprising the steps of:

(a) culturing the microbial host cell of claim 17 under conditions giving rise to the expression of the encoding sequence for exo-polygalacturonase therein, and (b) recovering the polypeptide having exo-polygalacturonase activity.

* * * * *